United States Patent
Lake et al.

(10) Patent No.: US 11,292,769 B2
(45) Date of Patent: Apr. 5, 2022

(54) PROCESS FOR MANUFACTURING A CYCLIC UREA ADDUCT OF AN ETHYLENEAMINE COMPOUND

(71) Applicant: NOURYON CHEMICALS INTERNATIONAL B.V., Arnhem (NL)

(72) Inventors: Karl Fredrik Lake, Södertälje (SE); Eike Nicolas Kantzer, Uddevalla (SE); Rolf Krister Edvinsson, Partille (SE); Ina Ehlers, Stenungsund (SE); Hendrik Van Dam, Ede (NL); Jenny Valborg Therese Adrian Meredith, Sweden (SE); Lars Torbjörn Hagberg, Stockholm (SE); Antoon Jacob Berend Ten Kate, Arnhem (NL); Rens Veneman, Amersfoot (NL); Michiel Jozef Thomas Raaijmakers, Deventer (NL); Slavisa Jovic, Utrecht (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 311 days.

(21) Appl. No.: 16/615,758

(22) PCT Filed: May 18, 2018

(86) PCT No.: PCT/EP2018/063044
§ 371 (c)(1),
(2) Date: Nov. 21, 2019

(87) PCT Pub. No.: WO2018/215326
PCT Pub. Date: Nov. 29, 2018

(65) Prior Publication Data
US 2021/0292282 A1   Sep. 23, 2021

(30) Foreign Application Priority Data
May 23, 2017 (EP) .................................. 17172487

(51) Int. Cl.
C07D 233/34   (2006.01)

(52) U.S. Cl.
CPC .................................. *C07D 233/34* (2013.01)

(58) Field of Classification Search
None
See application file for complete search history.

(56) References Cited

U.S. PATENT DOCUMENTS

| | | |
|---|---|---|
| 4,503,250 A | 3/1985 | Herdle |
| 4,897,480 A | 1/1990 | Schoenleben |
| 5,112,984 A | 5/1992 | Richey et al. |
| 9,440,928 B2 | 9/2016 | Gupta et al. |

FOREIGN PATENT DOCUMENTS

GB    877403 A   9/1961

OTHER PUBLICATIONS

Nomura, et al. "Carbonylation of amines by carbon dioxide in the presence of an organoantimony catalyst," Journal of Organic Chemistry, 1992, pp. 7339-7342, vol. 57, No. 26.
ISA-EPO, International Search Report and Written Opinion issued in International Application No. PCT/EP2018/063044, dated Jul. 2, 2018.

*Primary Examiner* — Clinton A Brooks
(74) *Attorney, Agent, or Firm* — Lorenz & Kopf, LLP

(57) ABSTRACT

Methods are provided for manufacturing a cyclic urea adduct of an ethyleneamine compound, the ethyleneamine compound being selected from the group of ethyleneamines and hydroxyethylethyleneamines and comprising at least one —NH—CH2-CH2-NH— moiety and at least two ethylene moieties, wherein the ethyleneamine compound is reacted with CO2 in the presence of an auxiliary compound selected from ethylenediamine (EDA), monoethanolamine (MEA) and mixtures thereof, the molar ratio of auxiliary compound to amine compound being at least 0.02:1. It has been found that the presence of an auxiliary compound selected from ethylenediamine (EDA), monoethanolamine (MEA) and mixtures thereof leads to a substantial increase of the reaction rate as compared to a process wherein the auxiliary compound is not present.

15 Claims, No Drawings

PROCESS FOR MANUFACTURING A CYCLIC UREA ADDUCT OF AN ETHYLENEAMINE COMPOUND

CROSS-REFERENCE TO RELATED APPLICATION

This application is a U.S. National-Stage entry under 35 U.S.C. § 371 based on International Application No. PCT/EP2018/063044, filed May 18, 2018, which was published under PCT Article 21(2) and which claims priority to European Application No. 17172487.5, filed May 23, 2017, which are all hereby incorporated in their entirety by reference.

TECHNICAL FIELD

The present invention is directed to a process for manufacturing a cyclic urea adduct of an ethyleneamine compound by reacting an ethyleneamine compound with CO2.

BACKGROUND

Ethyleneamines consist of two or more nitrogen atoms linked by ethylene units. Ethyleneamines can be present in the form of linear chains H2N(—CH2-CH2-NH)p-H. For p=1, 2, 3, 4, . . . this gives, respectively, ethylenediamine (EDA), diethylenetriamine (DETA), linear triethylenetetramine (L-TETA), and linear tetraethylenepentamine (L-TEPA). It is clear that this range can be extended. With three or more ethylene units it is also possible to create branched ethyleneamines such as N(—CH2-CH2-NH2)3, trisaminoethylamine (TAEA). Two adjacent ethylene units can be connected by two nitrogen atoms to form a piperazine ring HN((—CH2-CH2-)2)NH. Piperazine rings can be present in longer chains to produce the corresponding cyclic ethyleneamines.

Hydroxyethylethyleneamines comprise at least one hydroxyl group connected to a nitrogen atom through an ethylene unit, wherein the nitrogen atom is connected via a further ethylene group to an amino-group. An example is aminoethylethanolamine or AEEA of the formula H2N—CH2-CH2-NH—CH2-CH2-OH. Chain-extended ethanolamines include monoethanolamine compounds of the formula H2N—(CH2-CH2-NH)q-CH2-CH2-OH, wherein q is 2 or higher.

Ethyleneamine compounds which contain a linear —NH—CH2-CH2-NH— moiety can be converted into urea derivatives thereof through reaction with CO2. These urea derivatives comprise a cyclic ethylene urea unit of the following formula.

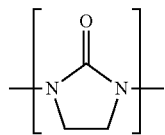

Ethyleneamine compounds comprising a cyclic ethylene urea unit can be used as starting material for chemical reactions, e.g., for the manufacture of chain-extended ethyleneamines or hydroxyethylethyleneamines. They may also be attractive products in themselves, e.g., for use in pesticides, pharmaceutical applications, and resins. In the present specification, ethyleneamine compounds comprising one or more cyclic ethylene urea units are also indicated as urea derivatives or urea adducts.

It has been found that converting ethyleneamine compounds comprising at least one linear —HN—CH2-CH2-NH— moiety and at least two ethylene moieties into their corresponding cyclic urea derivatives is not an easy process.

R. Nomura et al., Carbonylation of Amines by Carbon Dioxide in the Presence of an Organoantimony catalyst, J. Org. Chem. 1992, 57, 7339-7342 describes the formation of the cyclic urea UAEEA from AEEA and CO2 using exotic catalysts such as triphenylstibine oxide in the presence of tetraphosphorus decasulphide.

U.S. Pat. No. 4,897,480 describes a process for manufacturing N,N'-dialkylsubstituted cyclic urea derivatives by reacting a diamine with carbon dioxide in the gas phase in the presence of an oxide of, e.g., aluminium, or in the presence of an aluminium silicate or magnesium silicate.

There is need in the art for a process for converting ethyleneamine compounds selected from the group of ethyleneamines and hydroxyethylethyleneamines and comprising at least one linear —NH—CH2-CH2-NH— moiety and at least two ethylene moieties into their corresponding ethylene urea derivatives which process does not require the presence of metal-containing catalysts. The present invention provides a process which meets this need.

BRIEF SUMMARY

In an exemplary embodiment, a method for manufacturing a cyclic urea adduct of an ethyleneamine compound is provided. The ethyleneamine compound is selected from the group of ethyleneamines and hydroxyethylethyleneamines and comprises at least one —NH—CH2-CH2-NH— moiety and at least two ethylene moieties. The method includes reacting the ethyleneamine compound with CO2 in the presence of an auxiliary compound selected from ethylenediamine (EDA), monoethanolamine (MEA) and mixtures thereof, the molar ratio of auxiliary compound to amine compound being at least 0.02:1.

In another embodiment, a method to prepare ethylene amines or cyclic urea adducts thereof is provided. The method includes (a) manufacturing a cyclic urea adduct of an ethylene amine compound, the ethylene amine compound being selected from the group of ethylene amines and hydroxyethyl ethylene amines and comprising at least one —NH—CH2-CH2-NH-moiety and at least two ethylene moieties, wherein the ethylene amine compound is reacted with CO2 in the presence of an auxiliary compound selected from ethylene diamine (EDA), monoethanolamine (MEA) and mixtures thereof, the molar ratio of auxiliary compound to amine compound being at least 0.02:1. The method further includes (b1) where the cyclic urea adduct of an ethylene amine compound is a cyclic urea adduct of ethylene amine, reacting the cyclic urea adduct of ethylene amine with an ethanolamine-functional compound, or a urea- or carbamate additive thereof, or (b2) where the cyclic urea adduct of an ethylene amine compound is a cyclic urea adduct of a hydroxyethyl ethyleneamine, reacting the cyclic urea adduct of a hydroxyethyl ethyleneamine with a ethylene amine compound, or a urea- or carbamate additive thereof.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The invention pertains to a process for manufacturing a cyclic urea adduct of an ethyleneamine compound, the ethyleneamine compound being selected from the group of ethyleneamines and hydroxyethylethyleneamines and comprising at least one linear —NH—CH2-CH2-NH— moiety and at least two ethylene moieties, wherein the ethyleneamine compound is reacted with CO2 in the presence of an auxiliary compound selected from ethylenediamine (EDA), monoethanolamine (MEA) and mixtures thereof, the molar ratio of auxiliary compound to amine compound being at least 0.02:1.

It has been found that the presence of an auxiliary compound selected from ethylenediamine (EDA), monoethanolamine (MEA) and mixtures thereof leads to a substantial increase of the reaction rate as compared to a process wherein the auxiliary compound is not present. This makes it possible to dispense with the presence of a metal-containing catalyst and to perform the process under relatively mild conditions. Further advantages of the present invention and specific embodiments thereof will become clear from the further specification.

All numbers in this description indicating amounts, ratios of materials, physical properties of materials, and/or use are to be understood as modified by the word "about," except as otherwise explicitly indicated. The term "about" as used in connection with a numerical value and the claims denotes an interval of accuracy, familiar and acceptable to a person skilled in the art. In general, such interval of accuracy is ±10%. The invention will be discussed in more detail below.

The ethyleneamine compound used as starting material in the present invention is an ethyleneamine compound selected from the group of ethyleneamines and hydroxyethylethyleneamines and comprising at least one linear —NH—CH2-CH2-NH— moiety and at least two ethylene moieties.

The —NH—CH2-CH2-NH— moiety is linear, which means that it is not part of a piperazine ring. This is because —NH—CH2-CH2-NH— moieties in a piperazine ring cannot be converted to cyclic ethylene urea units of the following formula

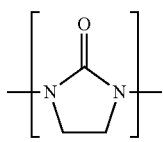

as this would require ring-opening.

The ethyleneamine compound comprises at least two ethylene moieties. This is because H2N—CH2-CH2-NH2, ethylenediamine, while having a —NH—CH2-CH2-NH— moiety does require the benefit of the present invention.

The at least two ethylene moieties are calculated on the total ethyleneamine compound molecule. Therefore, of the at least two ethylene moieties one is present in the —NH—CH2-CH2-NH— moiety, leaving at least one further ethylene moiety. The at least one further ethylene moiety may be present in one or more further —NH—CH2-CH2-NH— moieties. The at least one further ethylene moiety can also be present between two —NH—CH2-CH2-NH-moieties, or between a N-atom and an NH2 or OH group.

Examples of ethyleneamines which are suitable for use in the present invention include linear ethyleneamine compounds having at least one —NH—CH2-CH2-NH— moiety and at least two ethylene moieties. Compounds within this group are compounds of the formula H2N—(CH2-CH2-NH)p-H, wherein p is at least 2, in particular between 2 and 10. Examples of suitable compounds thus include diethylenetriamine (DETA) wherein p is 2, triethylenetetramine (L-TETA), wherein p is 3, and tetraetylenepentamine (L-TEPA), wherein p is 4.

The compounds may also include piperazine rings, where two nitrogen atoms are connected to each other via two ethylene groups. This does, however, not detract from the requirement that the compound should comprise at least one —NH—CH2-CH2-NH— moiety.

Examples of suitable piperazine-containing compounds are
piperazinoethyl ethylenediamine (PEEDA),

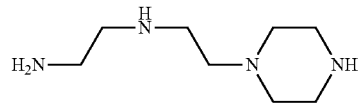 [SMILES: NCCNCCN1CCNCC1]

piperazinoethyl diethylenetriamine (PEDETA),

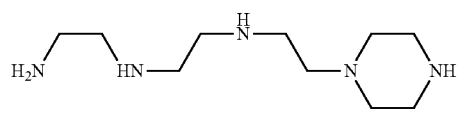 [SMILES: NCCNCCNCCN1CCNCC1]

aminoethylpiperazinoethyl ethylenediamine (AEPEEDA)

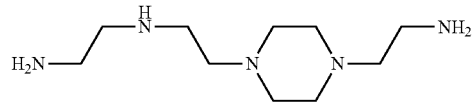 [SMILES: NCCNCCN1CCN(CCN)CC1]

The compounds may also include branched structures with tertiary nitrogen atoms. Again, this does not detract from the requirement that the compound should comprise at least one —NH—CH2-CH2-NH— moiety.

Where the ethyleneamine compound is an ethyleneamine, diethylenetriamine (DETA) and triethylenetetramine (L-TETA) are preferred because they result in attractive urea derivatives.

Examples of suitable branched compounds include aminoethyltriethylenetetramine (AETETA)

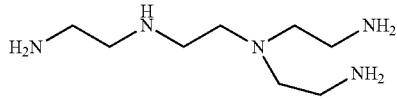 [SMILES: NCCNCCN(CCN)CCN]

Examples of hydroxyethylethyleneamines which are suitable for use in the present invention include linear hydroxyethylethyleneamine compounds having at least one —NH—CH2-CH2-NH— moiety and at least two ethylene moieties. Compounds within this group are compounds of the formula HO—CH2-CH2-NH—(CH2-CH2-NH)q-H, wherein q is at least 1, in particular between 1 and 10. Examples of suitable compounds thus include aminoethylethanolamine (AEEA), where q is 1, and 2-[[2-[(2-aminoethyl)amino]ethyl]amino]-ethanol, also indicated as hydroxyethyldiethylenetriamine (HE-DETA), where q is 2. As for the ethyleneamines discussed above, the compounds may comprise piperazine entities or tertiary amine groups, as long as the compound still comprises at least one —NH—CH2-CH2-NH-moiety.

Where the ethyleneamine compound is a hydroxyethylethyleneamine, the use of aminoethylethanolamine (AEEA) and hydroxyethyl diethylenetriamine (HE-DETA) is considered preferred.

In the process according to the invention, the ethyleneamine compound is reacted with CO2 in the presence of an auxiliary compound selected from ethylenediamine (EDA), monoethanolamine (MEA) and mixtures thereof, the molar ratio of auxiliary compound to amine compound being at least 0.02:1.

The amount of auxiliary compound can vary within wide ranges. The auxiliary compound can be present in catalytic amounts, with a minimum for the molar ratio of auxiliary compound to amine compound being at least 0.02:1. If less than this amount is present, the effect of the present invention will be too low for it to be of practical importance. It may be preferred for the molar ratio of auxiliary compound to amine compound to be at least 0.05:1, in particular at least 0.1:1.

The upper limit for the molar ratio molar ratio of auxiliary compound to amine compound is not critical, and may depend on the context in which the process is to be carried out. In general, an upper limit of 10:1 may be mentioned.

If the process is intended for the production of urea compounds as such, it may be desirable to remove the auxiliary compound at the end of the process. In this case, it may be attractive to limit the amount of auxiliary compound to a molar ratio per mole of amine compound of at most 2:1, in particular at most 1:1.

On the other hand, if the process is carried out as a preliminary step for reacting the auxiliary compound with the amine compound, the ratio between the two compounds may be governed by the desirable ratio for this further process. In this case it may be preferred for the molar ratio between the auxiliary compound and the amine compound to be at least 0.5:1 and/or at most 10:1, in particular at most 5:1. This embodiment will be discussed in more detail below.

The reaction with CO2 is carried out by bringing the mixture of ethyleneamine compound and auxiliary compound into contact with CO2 under reaction conditions.

Reaction conditions for forming a urea compound include a reaction temperature which generally is at least 120° C. At a temperature below 120° C., the reaction rate generally is too low to allow meaningful conversion within a reasonable time frame. It may be preferred for the reaction temperature to be at least 140° C., in particular at least 150° C., more in particular at least 170° C. The reaction is generally carried out at a temperature of at most 400° C. Due to the presence of the auxiliary compound, lower temperatures can be applied while still obtaining meaningful conversion within a reasonable time frame. The temperature may thus be at most 350° C., in particular at most 300° C., more in particular at most 250° C. or even at most 220° C. Operating at a temperature of 170-250° C. or 170-220° C. is considered preferred.

The pressure during the reaction is determined for the major part by the provision of CO2 to the reaction medium, with the total pressure in the system decreasing during the reaction due to the consumption of CO2. In general, the total pressure in the system is at most 100 bar, in particular at most 75 bar. The total pressure generally is at least 2 bar, in particular at least 5 bar, more in particular at least 10 bar.

The amount of CO2 provided to the reaction is not critical. The minimum amount is governed by the amount required to convert the amine compound into its corresponding urea adduct. Therefore, the molar ratio between CO2 and —NH—CH2-CH2-NH— moieties in the amine compound generally is at least 0.1:1. A ratio of at least 0.2:1, in particular at least 0.5:1 may be more attractive if more urea adduct is aimed for. A large excess of CO2 is not detrimental to the process, but is generally less attractive for economic reasons. Therefore, as a general maximum a value of 500:1 may be mentioned. The amount of CO2 dosed will depend on the desired amount of urea adduct in the final product.

The use of the auxiliary compound increases the reaction rate, and thus decreases the time required to obtain the desired degree of conversion. It is considered preferred for the reaction time to be at most 10 hours, in particular at most 6 hours, more in particular at most 3 hours. Very short reaction times may suffice. In general, the reaction time is at least 5 minutes. A reaction time between 0.5 and 2 hours may be particularly preferred.

The process according to the invention can be carried out in the absence of a metal-containing catalyst. Within the context of the present specification a catalyst is intended to refer to a component which is capable of increasing the rate of reaction in which the ethyleneamine compound is converted into its corresponding urea derivative.

At the start of the reaction, a reaction mixture is prepared comprising the ethyleneamine compound and the auxiliary compound. The reaction mixture may comprise further compounds which are either present to obtain an effect, or which are present as a result of previous processing steps. It is preferred for the reaction mixture to consist of at least 60 wt. % of the total of ethyleneamine compound and auxiliary compound, as the presence of further compounds generally does not benefit the reaction. It may thus be preferred for the reaction mixture to consist of at least 75 wt. % of the total of ethyleneamine compound and auxiliary compound, in particular at least 85 wt. %, more in particular at least 90 wt. %.

As the presence of water does not benefit the reaction, it is preferred for the reaction mixture comprising the ethyleneamine compound and the auxiliary compound to comprise at most 30 wt. % of water at the start of the reaction, in particular at most 10 wt. %, more in particular at most 5 wt. %.

The reaction generates the urea derivatives of the ethyleneamine compounds. During the reaction, the —NH—CH2-CH2-NH— group in the ethyleneamine starting compound is converted to a cyclic ethylene urea unit of the formula

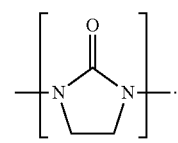

For example, diethylenetriamine (DETA) is converted to the urea derivative UDETA, triethylenetetramine (L-TETA) is converted to one or more urea derivatives UTETAs, tetraetylenepentamine (L-TEPA) is converted to one or more urea derivatives UTEPAs, aminoethylethanolamine (AEEA) is converted to the urea derivative UAEEA, and hydroxyethyldiethylenetriamine (HE-DETA) is converted to its urea derivative HE-UDETA. Piperazinoethylethylenediamine (PEEDA) is converted to its urea derivative UPEEDA. As will be evident to the skilled person, compounds with two distinct —NH—CH2-CH2-NH— groups can form di-urea additives. An example is the di-urea additive of linear triethylenetetramine (DUTETA). Some of the cited compounds are illustrated below:

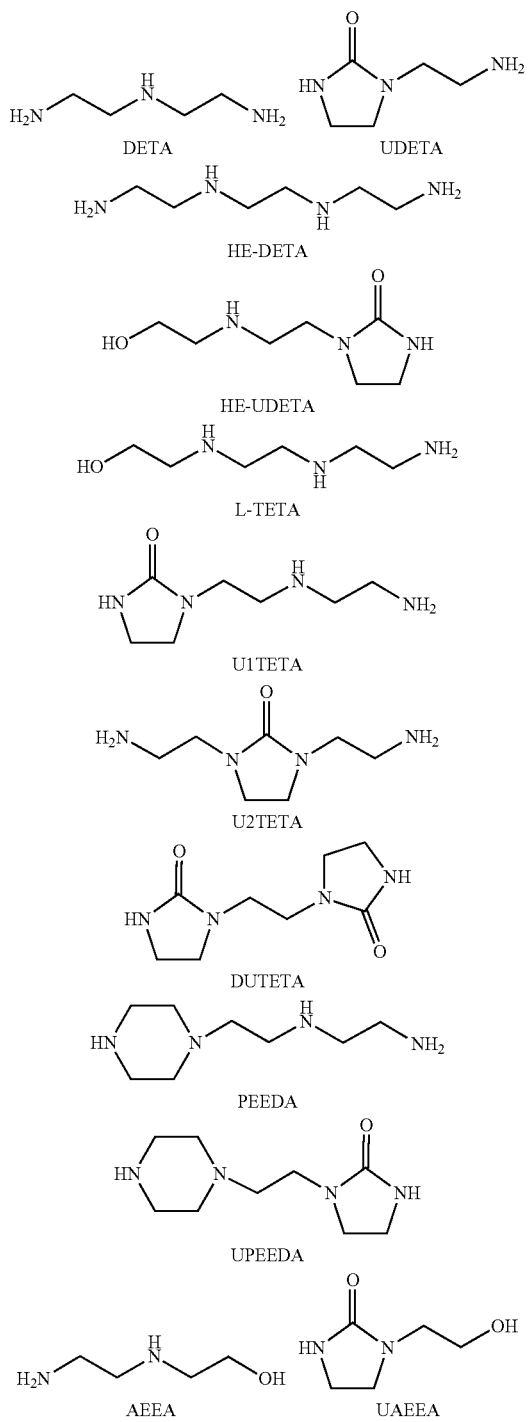

The auxiliary compounds monoethanolamine and ethylenediamine can also form CO-adducts. In the case of monoethanolamine this results in the formation of its carbamate additive 2-oxazolidone, also indicated as CMEA. In the case of ethylenediamine this results in the formation of ethylene urea, also indicated as EU. These compounds are presented below.

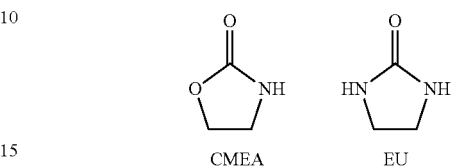

When the reaction is completed, the auxiliary compound, or its CO adduct, can be removed from the reaction mixture, if so desired. For example, as the auxiliary compounds have lower boiling points than the respective urea derivatives and the ethylene amines, the auxiliary compound can easily be removed through evaporation.

It has been found that the present invention is particularly suitable for the manufacture of a starting composition for manufacturing higher ethyleneamines or urea derivatives thereof.

For example, U.S. Pat. No. 4,503,250 describes a process for the manufacture of predominantly linear polyalkylene polyamines which comprises reacting ammonia or an alkyleneamine compound having two primary amino groups or mixtures thereof with an alcohol or an alkanolamine compound having a primary amino group and a primary or secondary hydroxyl group or mixtures thereof in the presence of a derivative of carbonic acid at a temperature at which the reaction will proceed under pressures sufficient to maintain the reaction mixture substantially in a liquid phase. The derivative of carbonic acid may be a urea compound.

Previously filed non-prepublished international application EP2017/052946 describes a process to prepare ethyleneamines of the formula NH2-(CH2-CH2-NH-)pH wherein p is at least 3 or derivatives thereof wherein one or more units —NH—CH2-CH2-NH— may be present as a cyclic ethylene urea unit or between two units —NH—CH2-CH2-NH— a carbonyl moiety is present, by reacting an ethanolamine-functional compound, an amine-functional compound in the presence of a carbon oxide delivering agent, wherein the molar ratio of carbon oxide delivering agent to amine-functional compound is at least 0.6 to 1.

Previously filed non-prepublished international application EP2017/052948 describes a process to prepare ethyleneamines of the formula NH2-(CH2-CH2-NH-)pH wherein p is at least 3 or derivatives thereof wherein one or more units —NH—CH2-CH2-NH— may be present as a cyclic ethylene urea unit or between two units —NH—CH2-CH2-NH— a carbonyl moiety is present, by reacting an ethanolamine-functional compound, an amine-functional compound in the presence of a carbon oxide delivering agent, wherein the molar ratio of ethanolamine-functional compound to amine-functional compound is at least 0.7:1 and the molar ratio of carbon oxide delivering agent to amine-functional compound is at least 0.05:1.

Previously filed non-prepublished international application EP2017/052945 describes a process to prepare ethyleneamines of the formula NH2-(CH2-CH2-NH-)pH wherein p is at least 2 wherein one or more units —NH—CH2-CH2-NH— are present as a piperazine unit or precursors thereof wherein optionally one or more units —NH—CH2-CH2-NH— are present as a cyclic ethylene urea unit or between two units —NH—CH2-CH2-NH— a carbonyl moiety is present, by reacting an ethanolamine-functional compound with an amine-functional compound in the presence of a carbon oxide delivering agent, wherein at least one of the amine-functional compound or the ethanolamine-functional compound contains a piperazine unit, and the reaction is performed in a liquid that comprises water.

In all applications it is indicated that the ethanolamine-functional compound and the carbon oxide delivering agent can be added in the form of a single compound. The amine-functional compound and the carbon oxide delivering agent can also be added in the form of a single compound. The present invention makes it possible to prepare starting compounds which are urea derivatives of amine-functional compounds or of ethanolamine compounds, which are suitable for use as starting material in the manufacture of higher ethyleneamines or urea derivatives thereof.

Therefore, in one embodiment, the invention pertains to a process for preparing ethyleneamines or urea derivatives thereof, which process comprises the steps of
a) manufacturing a cyclic urea adduct of an ethyleneamine compound, the ethyleneamine compound being selected from the group of ethyleneamines and hydroxyethylethyleneamines and comprising at least one linear —NH—CH2-CH2-NH— moiety and at least two ethylene moieties, wherein the ethyleneamine compound is reacted with CO2 in the presence of an auxiliary compound selected from ethylenediamine (EDA), monoethanolamine (MEA) and mixtures thereof, the molar ratio of auxiliary compound to amine compound being at least 0.02:1, and
b1) where the cyclic urea adduct of an ethyleneamine compound is a cyclic urea adduct of ethyleneamine, reacting the cyclic urea adduct of ethyleneamine with an ethanolamine-functional compound, or a urea- or carbamate additive thereof, or
b2) where the cyclic urea adduct of an ethyleneamine compound is a cyclic urea adduct of a hydroxyethylethyleneamine, reacting the cyclic urea adduct of a hydroxyethylethyleneamine with an ethyleneamine compound, or a urea- or carbamate additive thereof.

The manufacture of ethyleneamines by the process described above is in essence the reaction between an ethyleneamine compound and an ethanol amine compound wherein either compound can be at least partially in the form of a urea derivative, wherein the urea derivative is prepared by the process of step a), making use of the specified auxiliary compound. The description of the reaction as provided above will thus also apply to step a) of this process.

A particularly attractive embodiment of this process is one where in step b1 or b2 a reaction is envisaged with monoethanol amine or ethylenediamine. In that case, the auxiliary compound in step a) can be identical to one of the reactants used in step b1 or b2.

In a first embodiment, where monoethanol amine is used as reactant/auxiliary compound, the invention thus pertains to a process to prepare ethyleneamines or urea derivatives thereof which process comprises the steps of
a) manufacturing a cyclic urea adduct of an ethyleneamine compound, the ethyleneamine compound being selected from the group of ethyleneamines comprising at least one —NH—CH2-CH2-NH— moiety and at least two ethylene moieties, wherein the ethyleneamine compound is reacted with CO2 in the presence of monoethanolamine (MEA), the molar ratio of monoethanolamine to amine compound being at least 0.02:1, and
b) reacting the cyclic urea adduct of ethyleneamine with monoethanolamine or the carbamate derivative thereof.

In this case, as the auxiliary compound in step a) and the reactant in step b) are the same, it is preferred for the molar ratio of monoethanolamine to amine compound to be at least 0.1:1, in particular at least 0.2:1, more in particular at least 0.5:1, depending on the number of active groups in the amine compounds. As a maximum value, a molar ratio of 10:1 may be mentioned.

In a second embodiment, where ethylenediamine is used as reactant/auxiliary compound, the invention pertains to a process to prepare ethyleneamines or urea derivatives thereof, which process comprises the steps of
a) manufacturing a cyclic urea adduct of an ethyleneamine compound, the ethyleneamine compound being selected from the group of hydroxyethylethyleneamines comprising at least one —NH—CH2-CH2-NH— moiety and at least two ethylene moieties, wherein the ethyleneamine compound is reacted with CO2 in the presence of ethylenediamine (EDA), the molar ratio of ethylenediamine to amine compound being at least 0.02:1, and
b) reacting the cyclic urea adduct of hydroxyethylethyleneamine with ethylenediamine or the urea derivative thereof.

In this case, as the auxiliary compound in step a) and the reactant in step b) are the same, it is preferred for the molar ratio of ethylenediamine to amine compound to be at least 0.1:1 in particular at least 0.2:1, more in particular at least 0.5:1, depending on the number of active groups in the amine compounds. As a maximum value, a molar ratio of 10:1 may be mentioned.

Step b (whether b1 or b2) is preferably performed at a temperature of at least 100° C. The temperature should preferably be lower than 400° C. More preferably the temperature is between 200 and 360° C. Even more preferably the temperature is between 230 and 350° C. Most preferably the temperature is between 250 and 320° C. In embodiments where the ethanolamine-functional compound is monoethanolamine the most preferred temperature range is between 210 and 290° C., in particular between 230 and 290° C.

In step b the reaction time is in an embodiment between 5 minutes and 15 hours, preferably between 0.5 and 10 hours, more preferably between 1 and 6 hours.

As will be evident to the skilled person, preferred embodiments of various aspects of the present invention can be combined, unless they are mutually exclusive.

In the present specification, mention is made of urea adducts and urea derivatives. These terms are used interchangeably to refer to compounds wherein two nitrogen atoms are connected through a —C(O)— moiety. The terms CO adducts and CO2 adducts are also used interchangeably. They refer to compounds wherein either two nitrogen atoms are connected through a —C(O)— moiety or a nitrogen atom and an oxygen atom are connected through a —C(O)— moiety.

The present invention will be elucidated by the following examples, without being limited thereto or thereby.

Example 1: Comparison of Different Types of Auxiliary Compounds

To investigate the effect of various auxiliary compounds on the conversion of aminoethylethanolamine (AEEA) into its cyclic urea adduct, a number of experiments were carried out.

AEEA was combined with CO2 and the amine additive, if used, at a temperature of 190° C., and the mixture was kept at that temperature for 120 minutes. Then, the reaction mixture was cooled down and analyzed using GC-FID, which stands for gas chromatography using a flame ionization detector, using an internal standard.

The results are given in Table 1. Examples 1.A through 1.D are comparative. In Example 1.A no additive is used. In examples 1.B, 1.C, and 1.D, additives were used which are not in accordance with the present invention, namely 1,3-diaminopropane (PDA), aminoethyl piperazine (AEP), and piperazine (PIP). Examples 1.1 and 1.2 are according to the invention. In both cases ethylenediamine is used as additive. In Example 1 the molar ratio of EDA to AEEA was 1:1. In Example 2 the molar ratio of EDA to AEEA was 0.2:1.

TABLE 1

| Example | 1.A | 1.B | 1.C | 1.D | 1.1 | 1.2 |
|---|---|---|---|---|---|---|
| Additive | No | PDA | AEP | PIP | EDA | EDA |
| mole additive/mol AEEA | 0 | 1 | 1 | 1 | 1 | 0.2 |
| mole CO2 on (AEEA + additive) | 1 | 1 | 1 | 1 | 1 | 1 |
| Conversion of AEEA (wt. %, calculated on starting AEEA) | 89 | 89 | 85 | 82 | 98 | 94 |
| Selectivity to UAEEA (wt. %, calculated on consumed AEEA) | 96 | 97 | 92 | 85 | 93 | 99 |

As can be seen from table 1, Example A carried out in the absence of additive resulted in a conversion of AEEA of 89% into UAEEA, and a selectivity to UAEEA of 96%. The addition of 1,3-diaminopropane (PDA), aminoethyl piperazine (AEP), or piperazine (PIP) did not result in improved conversion or selectivity. The addition of 1 mole ethylenediamine per mole AEEA increased the conversion to a value of 98%. The use of 0.2 mole ethylenediamine per mole AEEA gave rise to an increase in both conversion and selectivity.

Example 2: Influence of EDA on the Reaction Rate

To investigate the effect of EDA on the reaction rate, the conversion of AEEA in the presence and absence of EDA was investigated over time. The process was carried out as described in Example 1. The reaction temperature was 190° C. In both cases the reaction mixture was at the same excess CO2 pressure at the beginning of the reaction (about 1.6 mole CO2 per mole AEEA+additive). The results are presented in Table 2. The analysis was carried out using GC-FID.

TABLE 2

| Example | 2.A | 2.1 |
|---|---|---|
| Additive | — | EDA |
| mole additive/mol AEEA | 0 | 1 |
| conversion after 30 minutes (wt. %) | 55 | 75 |
| conversion after 60 minutes (wt %) | 78 | 98 |
| conversion after 120 minutes (wt. %) | 88 | 100 |

As can be seen from Table 2, the presence of EDA resulted in a substantial increase in the reaction rate.

Example 3: Influence of Reaction Temperature

To investigate the influence of reaction temperature, the reaction was carried out at different temperatures. The process was carried out as described in Example 2 (about 1.7 mole CO2 per mole AEEA+additive). One mole EDA was used per mole AEEA. The reaction was continued for 120 minutes. The analysis was carried out using GC-FID. The results are presented in Table 3.

TABLE 3

| Example | 3.1 | 3.2 | 3.3 |
|---|---|---|---|
| Additive | EDA | EDA | EDA |
| Temperature (° C.) | 170 | 180 | 190 |
| AEEA conversion (wt. %) | 71 | 94 | 100 |

As can be seen from Table 3, a reaction temperature of 190° C. makes for 100% AEEA conversion after 120 minutes. At lower temperatures, the conversion after 120 minutes decreases. Nevertheless, even at 170° C. substantial AEEA conversion is obtained.

Example 4: Monoethanolamine and Ethylenediamine in the Conversion of Diethylenetriamine The influence of monoethanolamine and ethylenediamine on the conversion of diethylenetriamine was investigated.

Diethylenetriamine (DETA) was combined with the auxiliary compound, if used, and CO2 in a reaction vessel at reaction temperature, and kept at that temperature for 30 minutes. In all cases 1.3 mole of CO2 was used per mole of DETA. The auxiliary compound was monoethanolamine (MEA) or ethylenediamine (EDA), or no additive was added. Then, the reaction mixture was cooled down and analysed using GC-FID.

The results are presented in Table 4 below:

TABLE 4

| Example | 4.A | 4.1 | 4.2 |
|---|---|---|---|
| Reactants | DETA | DETA | DETA |
| Additive (molar ratio on DETA) | — | 0.2 MEA | 0.2 EDA |
| T (° C.) | 190 | 190 | 190 |
| t (min) | 30 | 30 | 30 |
| DETA Conversion (wt. %) | 70 | 95 | 77 |

As can be seen, the addition of MEA or EDA gives rise to a substantial increase in DETA conversion as compared to the experiment carried out in the absence of MEA and EDA.

Example 5: Monoethanolamine in the Conversion of Aminoethylethanolamine

The influence of monoethanolamine on the conversion of aminoethylethanolamine was investigated.

Aminoethylethanolamine (AEEA) was combined with the auxiliary compound, if used, and the mixture was saturated with CO2 in a reaction vessel (about 1.5 mole equivalents of CO2 per mole AEEA+additive). The reaction temperature was maintained for 30 minutes. The auxiliary compound was monoethanolamine (MEA), or no additive was added. Then, the reaction mixture was cooled down and analysed using GC-FID.

The results are presented in Table 5 below:

TABLE 5

| Example | 5.A | 5.1 |
|---|---|---|
| Reactants | AEEA | AEEA |
| Additive (molar ratio on AEEA) | — | 1.0 MEA |
| T (° C.) | 190 | 190 |
| t (min) | 30 | 30 |
| AEEA Conversion (wt. %) | 55 | 76 |

As can be seen, the addition of MEA gives rise to a substantial increase in AEEA conversion as compared to the experiment carried out in the absence of MEA.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for manufacturing a cyclic urea adduct of an ethyleneamine compound, the ethyleneamine compound being selected from the group of ethyleneamines and hydroxyethylethyleneamines and comprising at least one NH—CH2-CH2-NH— moiety and at least two ethylene moieties, wherein the method comprises:
reacting the ethyleneamine compound with $CO_2$ in the presence of an auxiliary compound selected from ethylenediamine (EDA), monoethanolamine (MEA) and mixtures thereof, the molar ratio of auxiliary compound to amine compound being at least 0.02:1.

2. The method according to claim 1, wherein the ethyleneamine compound is selected from diethylenetriamine (DETA), triethylenetetramine (L-TETA), aminoethylethanolamine (AEEA), and hydroxyethyldiethylenetriamine (HE-DETA).

3. The method according to claim 1, wherein the molar ratio of auxiliary compound to amine compound is at least 0.05:1.

4. The method according to claim 1, wherein the reaction is carried out at a temperature of at least 120° C. and at most 400° C.

5. The method according to claim 1, wherein the molar ratio between CO2 and —NH—CH2-CH2-NH— moieties in the amine compound is at least 0.5:1 and at most 500:1.

6. The method according to claim 1, wherein the reaction time is at most 10 hours.

7. A method to prepare ethylene amines or cyclic urea adducts thereof, the method comprising the steps of
a) manufacturing a cyclic urea adduct of an ethylene amine compound, the ethylene amine compound being selected from the group of ethylene amines and hydroxyethyl ethylene amines and comprising at least one —NH—CH2-CH2-NH— moiety and at least two ethylene moieties, wherein the ethylene amine compound is reacted with CO2 in the presence of an auxiliary compound selected from ethylene diamine (EDA), monoethanolamine (MEA) and mixtures thereof, the molar ratio of auxiliary compound to amine compound being at least 0.02:1, and
b1) where the cyclic urea adduct of an ethylene amine compound is a cyclic urea adduct of ethylene amine, reacting the cyclic urea adduct of ethylene amine with an ethanolamine-functional compound, or a urea- or carbamate additive thereof, or
b2) where the cyclic urea adduct of an ethylene amine compound is a cyclic urea adduct of a hydroxyethyl ethyleneamine, reacting the cyclic urea adduct of a hydroxyethyl ethyleneamine with a ethylene amine compound, or a urea- or carbamate additive thereof.

8. The method according to claim 7, which comprises the steps of
a) manufacturing a cyclic urea adduct of an ethylene amine compound, the ethylene amine compound being selected from the group of ethylene amines comprising at least one —NH—CH2-CH2-NH— moiety and at least two ethylene moieties, wherein the ethylene amine compound is reacted with $CO_2$ in the presence of monoethanolamine (MEA), the molar ratio of monoethanolamine to amine compound being at least 0.02:1, and
b) reacting the cyclic urea adduct of ethylene amine with monoethanolamine or the carbamate derivative thereof.

9. The method according to claim 8, wherein the molar ratio of monoethanolamine to amine compound is at least 0.1:1.

10. The method according to claim 8, wherein step b, b1, or b2 is performed at a temperature of at least 100° C. and lower than 400° C.

11. The method according to claim 7, which comprises the steps of
a) manufacturing a cyclic urea adduct of an ethylene amine compound, the ethylene amine compound being selected from the group of hydroxyethyl ethylene amines comprising at least one —NH—CH2-CH2-NH— moiety and at least two ethylene moieties, wherein the ethylene amine compound is reacted with $CO_2$ in the presence of ethylene diamine (EDA), the molar ratio of ethylene diamine to amine compound being at least 0.02:1, and
b) reacting the cyclic urea adduct of hydroxyethyl ethylene amine with ethylene diamine or the urea derivative thereof.

12. The method according to claim 11, wherein the molar ratio of ethylene diamine to amine compound is at least 0.1:1.

13. The method according to claim 7 wherein the ethylene amine compound is selected from diethylenetriamine (DETA), triethylenetetramine (TETA), aminoethylethanolamine (AEEA), and hydroxyethyldiethylenetriamine (HE-DETA).

14. The method according to claim 7, wherein step a) is carried out at a temperature of at least 120° C. and at most 400° C.

15. The method according to claim 7, wherein the reaction time in step a) is at most 10 hours and at least 5 minutes.

* * * * *